United States Patent [19]

Maryanoff et al.

[11] Patent Number: 4,908,450
[45] Date of Patent: Mar. 13, 1990

[54] CERTAIN HEXAHYDRO-6-ARYLPYRROLO[2,1-A]ISOQUINOLINES

[75] Inventors: Bruce E. Maryanoff; Cynthia A. Maryanoff, both of Solebury Township, Bucks County; David F. McComsey, Warminster; Kirk L. Sorgi, Norristown, all of Pa.

[73] Assignee: McNeilab, Inc., Spring House, Pa.

[21] Appl. No.: 304,304

[22] Filed: Jan. 31, 1989

Related U.S. Application Data

[62] Division of Ser. No. 156,063, Feb. 16, 1988, Pat. No. 4,837,328.

[51] Int. Cl.⁴ .................. C07D 471/08; C07D 491/08; C07D 491/056
[52] U.S. Cl. ......................................... 546/94; 546/65
[58] Field of Search .................................. 546/94, 65

[56] References Cited

U.S. PATENT DOCUMENTS 4,595,688  6/1986  Maryanoff et al. ................. 514/285

OTHER PUBLICATIONS

Journal of Medicinal Chemistry, 1987, Vol. 30, No. 8, pp. 1, 2 and 4.
B. Maryanoff et al., Journal of Chemistry, 1981, 46, 355–360, p. 4.
Drugs of the Future 11(2):18–20 (1986), p. 7.
B. Maryanoff et al., Journal of Heterocyclic Chemistry, May–June, 1985, p. 9.
Angew. Chem. Int. Ed. Engl. 24 (1985) No. 11, p. 9.

Primary Examiner—Alan L. Rotman

[57] ABSTRACT

A diastereoselective process for known antidepressive compounds (I) via reduction of the corresponding alcohol (VII):

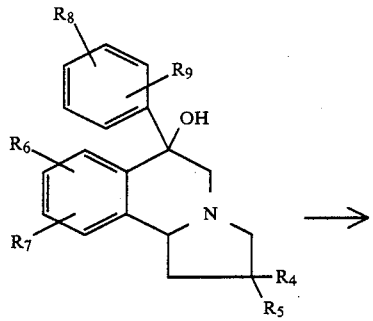

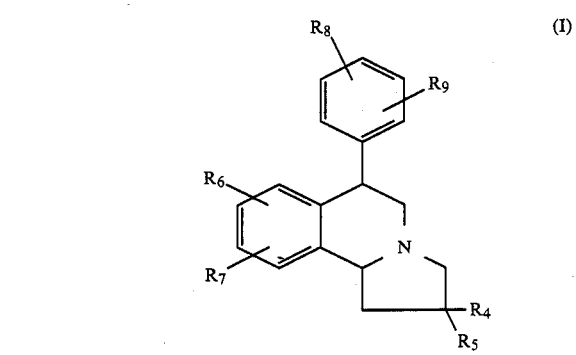

whereby the product mixture of diastereomers is surprisingly and unexpectedly rich in the content of the trans configuration (II) over the cis configuration (III) as defined in the following formulae:

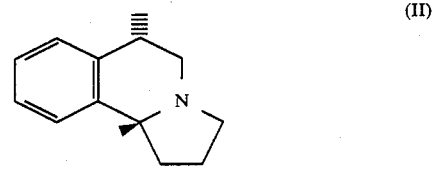

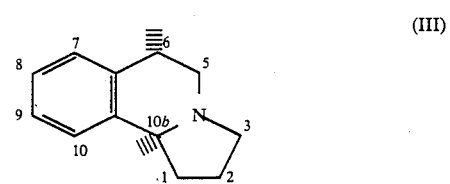

The preferred reaction conditions include use of a borane complex as the reducing agent and an acidic solvent such as trifuloroacetic acid.

2 Claims, No Drawings

CERTAIN HEXAHYDRO-6-ARYLPYRROLO[2,1-A]ISOQUINOLINES

This is a division of application Ser. No. 156,063, filed Feb. 16, 1988, U.S. Pat. No. 4,837,328.

BACKGROUND OF THE INVENTION

Hexahydro-6-aryl-pyrrolo[2,1-a]isoquinolines (I) comprise a very valuable class of compounds, in that they are useful for the treatment of depression in warm-blooded animals, e.g., man as disclosed in U.S. Pat. No. 4,595,688 to B. E. Maryanoff. Such compounds are of the following formula (I) and the pharmaceutically acceptable salts thereof:

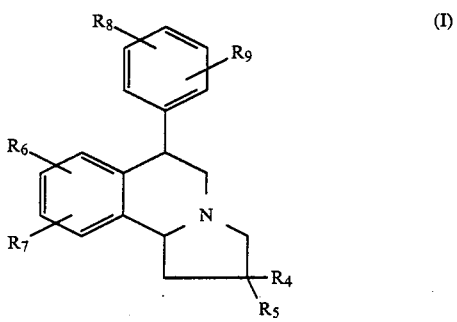

(I)

wherein
- $R_4$ and $R_5$ are the same and both are hydrogen, or different and each is selected from the group of hydrogen or lower alkyl, e.g. having 1 to 4 carbons;
- $R_6$ and $R_7$ are the same or different and each is selected from the group of hydrogen, lower alkyl, e.g. having 1 to 4 carbons, lower alkoxy, e.g. having 1 to 4 carbons, or halogen, or else are taken together as methylenedioxy; and
- $R_8$ and $R_9$ are selected from the group of hydrogen, lower alkyl, e.g. having 1 to 6 carbons, perfluoro(lower)alkyl, e.g. having 1 to 4 carbons, lower alkoxy, e.g. having 1 to 4 carbons, carb(lower)alkoxy, e.g. having 1 to 5 carbons, lower alkylthio, e.g. having 1 to 4 carbons, lower alkylsulfonyl, e.g. having 1 to 4 carbons, nitro or halogen.

A more detailed description of such compounds of formula (I) as well as methods for their synthesis and utility are described in U.S. Pat. No. 4,595,688 which is hereby incorporated by reference. The numbering system for the various substituents, e.g. $R_4$ and $R_5$, conform to that in the '688 patent $R_1$, $R_2$ and $R_3$ are missing from formula (I) since such positions in the '688 patent are only hydrogen herein.

The various diastereomers of each formula (I) compound are distinguished herein using the nomenclature recommended by Chemical Abstracts for representing the relative configuration of diastereomers of fused-ring compounds ($\alpha/\beta$ nomenclature). This requires that the stereocenter corresponding to the lowest numbered atom in the ring system (numbered according to convention) be designated $\alpha$ and that the remaining stereocenters be labeled $\alpha$ or $\beta$ relative to the first-assigned center. In this class of compounds, biological activity is generally found to be enhanced in one class of diastereomers in which the stereocenters at positions 6 and 10b are in a trans geometry ($6\alpha,10b\beta$ configuration), see Maryanoff, B. E., et al. J. Med. Chem 1987, 30, 1433. The trans ($6\alpha,10b\beta$) and cis ($6\alpha,10b\beta$) arrangements are shown in formula (II) and (III), respectively:

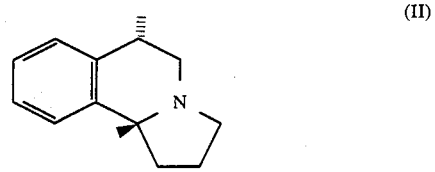

(II)

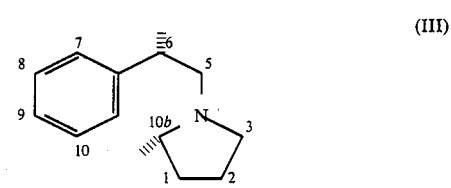

(III)

Also, biological activity is largely exhibited by one of the two possible enantiomers, that being the one with a R arrangement at the 10b position as shown in formula (II).

The various prior art synthesis methods for formula (I) compounds produce mixtures of diastereomers which are not highly enriched in the preferred trans diastereomer (II). For the compound of formula (I) where $R_4$, $R_5$, $R_6$ and $R_7$ are hydrogen, a most favorable ratio is only about 3:1 (trans:cis) by the hydrogenation of enamine (IV) in the presence of triethylamine. The product of the reaction is the mixture of the trans diastereomer (V) and the cis (VI):

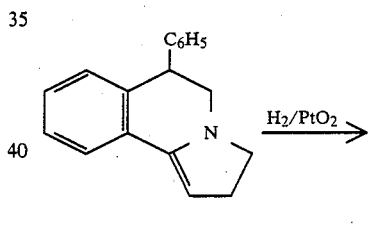

(IV)

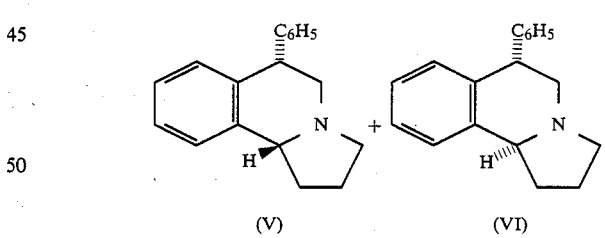

(V)     (VI)

Other prior art processes give poorer trans/cis ratios, ranging from 1:10 to 1:2

It is an object of the present invention to provide a new process that results in high diastereoselection of the more desirable trans isomer of formula (II).

SUMMARY OF THE INVENTION

The present invention comprises a new process for the preparation of hexahydro-6-arylpyrrolo[2,1-a]isoquinoline derivatives of formula (I) with high stereocontrol for the trans diastereomeric class of formula (II). The invention comprises the reduction of a 6-hydroxy compound of the following formula (VII) where $R_4$, $R_5$, $R_6$, $R_7$, $R_8$ and $R_9$ are as defined for formula (I) to yield a compound of formula (I) as the product:

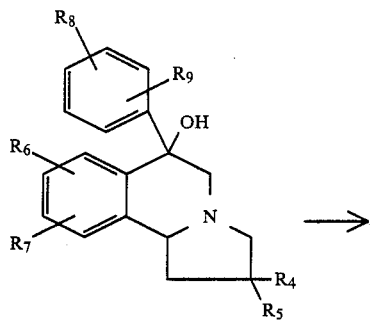
(VII)

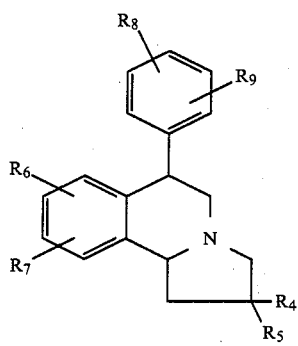
(I)

The reaction may be carried out in trifluoroacetic acid with a borane complex, such as borane-tetrahydrofuran, see Maryanoff, B. E., et al., J. Org. Chem. 1987, 45, 355. Second, this invention illustrates selective production of a particular enantiomer of (I) especially the more desired 10bR enantiomer, by employing enantiomerically enriched pyrrolidine (VIII) where $R_6$ and $R_7$ are as defined for formula (I) as a starting material:

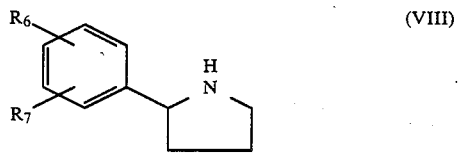
(VIII)

The pyrrolidine of formula (VIII) may be used to produce formula (I) compounds, e.g. via the Mandelic Acid Route (C) or Styrene Oxide Route (D) of U.S. Pat. No. 4,595,688.

DETAILED DESCRIPTION OF THE INVENTION

The invention comprises the deoxygenation of the amino alcohol (VII) or an acid-addition salt thereof to yield the amine (I):

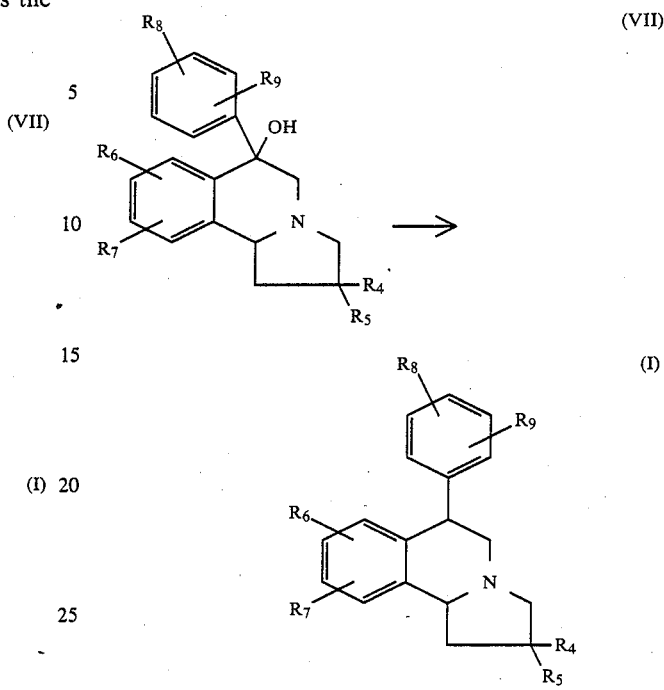

which has been found to occur in a highly diastereoselective fashion. In formulae (VII) and (I):

$R_4$ and $R_5$ are the same and both are hydrogen, or different and each is selected from the group of hydrogen or lower alkyl, e.g. having 1 to 4 carbons;

$R_6$ and $R_7$ are the same or different and each is selected from the group hydrogen, lower alkyl, e.g. having 1 to 4 carbons, lower alkoxy, e.g. having 1 to 4 carbons, hydroxy, or halogen, or else are taken together as methylenedioxy; and $R_8$ and $R_9$ are selected from the group of hydrogen, lower alkyl, e.g. having 1 to 6 carbons, perfluoro(lower)alkyl, e.g. having 1 to 4 carbons, lower alkoxy, e.g. having 1 to 4 carbons, carb(lower)alkoxy, e.g. having 1 to 5 carbons, lower alkylthio, e.g. having 1 to 4 carbons, lower alkylsulfonyl, e.g. having 1 to 4 carbons, nitro or halogen.

As used herein, the terms "lower alkyl", "lower alkoxy", "lower alkylthio", "lower alkylsulfonyl", and "perfluoro(lower)alkyl" refer to straight- or branched-chain carbon skeletons, within the carbon-atom limits defined. The term halo (or halogen) is generic for fluorine, chlorine, bromine, and iodine.

With the use of the invention process, the ratio of the two diastereomers (II) and (III) in the product of formula (I) is greater than about 1:1, e.g. greater than about 5:1, 9:1 or even 12:1 or 20:1.

The process of the invention is effected by placing amino alcohol (VII), or an acid-addition salt thereof, such as those from mineral acids HCl, HBr, HClO$_4$, HPF$_6$ and the like, into a strongly acidic solvent such as trifluoroacetic acid (TFA) or trifluoromethanesulfonic acid with or without an inert solvent such as methylene chloride and adding a reducing agent. In particular, the amino alcohol (VII), or salt thereof, is combined with TFA at temperatures between about −20° and 30° C., preferably at −10° to 10° C. The mixture preferably is maintained at −10° to 5° C. and treated with a reducing agent.

In particular, the reducing agent is chosen from the class of compounds known as borane complexes, such as borane-tetrahydrofuran, borane-methyl sulfide, borane-pyridine, borane-trimethylamine, and the like. Borane-tetrahydrofuran is particularly useful in this regard. The temperature of the reduction, −10° to 5° C., in this instance is critical to optimizing high diastereoselectivity for the trans form. Other reducing agents capable of converting an iminum salt to the corresponding amine in an acidic medium are also useful. Examples of these are metal borohydrides, particularly highly reactive, such as sodium trimethoxyborohydride and sodium borohydride. Thus, one obtains (I) with an enrichment in favor of the trans diastereomer as high as about 12:1 to 20:1. This high enrichment greatly facilitates separation of the more desirable trans isomer by crystallization procedures, as opposed to chromatographic procedures, and enhances the overall yield of the more desirable trans isomer.

The process is illustrated more particularly for the important compound trans-1,2,3,5,6,10b-hexahydro-6-[4-(methylthio)phenyl]-pyrrolo[2,1-a]isoquinoline of formula (I), in the (II) trans configuration, where $R_4$, $R_5$, $R_6$, $R_7$ and $R_8$ are hydrogen and $R_9$ is methylthio at the 4-position. This compound is also known as McN-5652-Z described by Maryanoff, B. E., et al. Drugs of the Future, 1986, 11,18.

As a particular example, the hydrochloride salt of a diastereomeric mixture of the compound of formula (VII) where $R_4$ $R_5$, $R_6$, $R_7$ and $R_8$ are hydrogen and $R_9$ is 4-methylthio is dissolved in TFA at −10° to 0° C. and treated with 1.5 mol equiv of borane-THF at −10° to 0° C. to produce a mixture of the corresponding compound of formula (I) in the (II) and (III) configurations that is enriched in desired (II) to the extent of 92–95%.

As an alternative, the highly diastereoselective reduction may be conducted in two stages by first dehydrating the amino alcohol (VII) to an unstable enamine, e.g. of the following formula (IX):

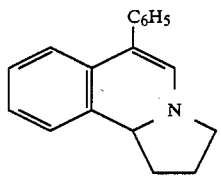

(IX)

The dehydration can be effected with polyphosphoric acid and/or trifluoroacetic acid, depending on the substituents present on the aromatic rings. The very air-sensitive, unstable enamine is immediately added to TFA and reduced with borane-THF to give final product (I) with a trans:cis ratio of about 3:1. Though this procedure is functional, it is generally not preferred.

Although the practice of the invention should not be bound by the present understanding of its course, the source of the high diastereoselectivity in the deoxygenation of formula (VII) is believed to be associated with dehydration of the substrate in the acidic medium to an N-protonated enammonium salt (X) and rearrangement of such species to an iminium salt of the following formula (XI) which may then be reduced with a reducing agent to yield the product of formula (I):

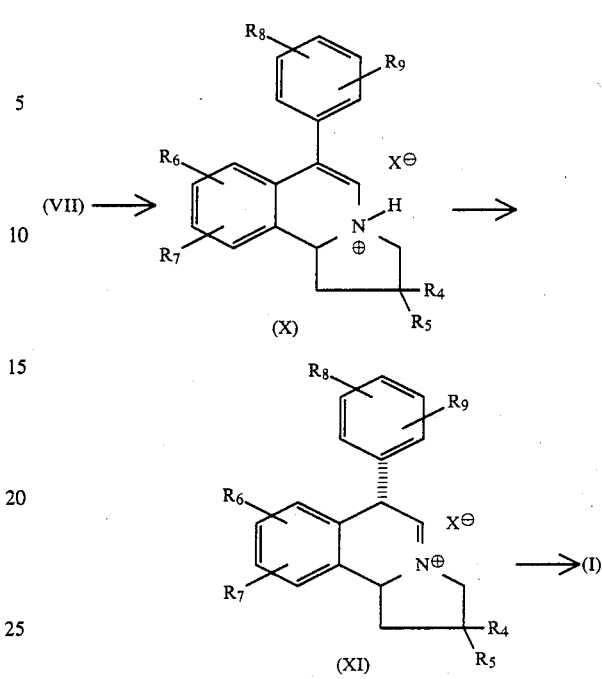

wherein $R_4$, $R_5$, $R_6$, $R_7$, $R_8$ and $R_9$ are as defined for formula (I) and X is an anion. Particular anions for X are the anions which would be present if the hydroxy starting material of formula (VII) is used as an acid-addition salt, or the anion which would be present when (VII) is introduced to a strongly acidic medium to yield the transitory intermediate enammonium salt (X) e.g. $CF_3COO^-$, $Cl^-$, $Br^-$, $I^-$, $PF_6^-$ or $BF_4^-$. It is in this proton shift or protonation in going from enammonium (X) to iminium (XI) that the crucial trans stereochemistry at the 6 and 10b positions is believed to be established. The iminium salt (XI) is then reduced to the desired product (I) with retention of the high trans enrichment prior to epimerization of the iminium species. Thus, the conditions for the enamine salt to iminium salt conversion must be monitored and evaluated, mainly in the sense that epimerization processes need to be avoided. Also, the reduction should be effected without epimerization of the iminium salt. The conditions of the process are thus important for optimal production of the product of formula (I) in the trans (II) configuration.

For an enantioselective, as opposed to merely a diastereoselective, synthesis of hexahydro-6-aryl-pyrrolo[2,1-a]isoquinoline derivatives, the 2-arylpyrrolidine (VIII) is resolved or prepared by enantioselective synthesis, e.g., Maryanoff and McComsey, J. Heterocyclic Chem. 1985, 22,911.

An example of an enantioselective synthesis of 2-arylpyrrolidines is given by H. Brunner, et al., Agnew. Chem. Int. Ed. Engl. 1985, 24, 995. This enantiomerically enriched pyrrolidine is then transformed into (VII), which is deoxygenated according to the invention to (I) by the synthetic process of this invention.

The invention will be further understood and appreciated by the following examples, which illustrate the preparation of compounds according to the invention. These examples serve to illustrate both diastereoselective and enantioselective syntheses. These examples also show the independence of the diastereoselective reduction process from the diastereomeric nature of the starting amino alcohols. These examples are given for the purpose of illustration and are not to be construed as limiting the invention in spirit or in scope.

In the following Examples and throughout the specification, the following abbreviations may be used: g (grams); mg (milligrams); mL (milliliters); L (liters); min (minutes); hr (hours); mmol (millimoles); mol (moles); N (normal); RT (room temperature); glc (gas-liquid chromatography); IPA (isopropyl alcohol); TFA (trifluoroacetic acid); and mp (melting point). Unless otherwise indicated, all temperatures are in °C. (degrees Centigrade).

EXAMPLES

Example A trans-1,2,3,5,6,10b-Hexahydro-6-[(4-methylthio)-phenyl]pyrrolo[2,1-a]isoquinoline (Formula (I), Configuration (II): $R_4$, $R_5$, $R_6$, $R_7$ and $R_8$=H; $R_9$=4-methylthio)

Under an inert atmosphere, 640 ml of TFA was cooled to −10° C. and 100 g (0.29 mol) of the aminoalcohol of formula (VII) where $R_4$,$R_5$,$R_6$, $R_7$ and $R_8$=H; and $R_9$=4-methylthio as the HCl salt was added portionwise over 15 min. The reaction mixture turned a dark purple color which slowly disappeared over 1 hr. While maintaining a −5° to −10° C. reaction temperature 500 mL (0.45 mol) $BH_3$.THF was added dropwise over 1.5 hr. The reaction was warmed to RT slowly over 1.5 hr, 500 mL of water was added, and it was stirred overnight. The mixture was poured into 1 L $CH_2Cl_2$ and washed with 1 L of water (2×) and 1 L of cold 3N NaOH (2×). The organic layer was dried with sodium sulfate and the solvents removed in vacuo to yield a slightly brown oil residue. The residue was dissolved in 1 L IPA and filtered through a pad of Celite. The filtrate was treated at RT with 41 g (0.29 mol) perchloric acid. After stirring and scratching for 1 hr the resultant slurry was cooled in an ice bath. The solid was filtered and the filter cake washed with cold IPA to afford 104.5 g (92%) of the title compound (McN-5652Z-perchlorate) as a greenish-white solid; mp=199.0°–201.0° C. GLC assay indicated that 8% of the unwanted cis isomer of configuration (III) was present.

Example B trans-1,2,3,5,6,10b-Hexahydro-6-phenyl pyrrolo[2,1-a]isoquinoline (Formula (I), configuration (II): $R_4$, $R_5$, $R_6$, $R_7$, $R_8$ and $R_9$=H B1: From cis-1,2,3,5,6,10b-Hexahydro-6-hydroxy-6-phenyl pyrrolo[2,1-a]isoquinoline (Formula (VII) configuration (III))

cis 1,2,3,5,6,10bα-Hexahydro-6β-phenylpyrrolo[2,1-a]isoquinoline-6α-ol (E)-Butenedioate (1:1) (50 mg, 0.13 mmol) was dissolved in 2 mL of TFA under argon at RT. The solution was cooled in an ice bath and 1M $BH_3$.THF (0.50 ml, 0.50 mml; Aldrich) was added and reaction stirred at 5° C. for 2 hr. The reaction was quenched with five drops of water and stirred at RT for 15 minutes, basified with 1N NaOH and extracted with methylene chloride. The organic solution was washed once with water, once with saturated NaCl, dried ($K_2CO_3$) and evaporated in vacuo to give a mixture of amine products (30 mg, 93%); glc showed a 93 to 7 ratio of trans/cis (II/III) amines. $^1$NMR verified the high proportion of trans isomer.

B2: From trans-1,2,3,5,6,10b-Hexahydro-6-hydroxy-6-phenyl pyrrolo [2,1-a]-isoquinoline hydrobromide (Formula (VII) configuration (II))

trans-1,2,3,5,6,10bβ-Hexahydro-6β-phenylpyrrolo [2,1-a]isoquinoline-6α-ol Hydrobromide (1:1) (30 mg, 0.087 mmol) was reacted in a manner identical to Example B1 to give an oily product mixture of amines (20 mg, 92%); glc showed an 86 to 14 ratio of trans/cis (II/III) amines and $^1$H NMR showed predominantly the trans isomer.

Example C

Reduction of Enamine trans-1,2,3,5,6,10bβ-Hexahydro-6β-phenylpyrrolo[2,1-a]-isoquinoline-6α-ol Hydrobromide (1:1) (200 mg, 0.58 mm) was combined with polyphosphoric acid (4.0 g) and heated at 100° C. with occasional stirring for 15 min. The reaction was diluted with water, made alkaline with 3N NaOH and extracted with $CH_2Cl_2$. The organic layer was washed once with water, dried ($K_2CO_3$) amd evaporated in vacuo to give a dark green oil of formula (IX) (100 mg, 69%). A portion (50 mg) was dissolved in 1 ml of TFA under argon, cooled to 5° C. and 1M $BH_3$•THF (0.5 ml, 0.50 mm) was added. After 60 min. at 5° C., the reaction was quenched with water, stirred 10 min and then made alkaline with 3N NaOH and extracted with $CH_2Cl_2$. The organic phase was dried ($K_2CO_3$) and evaporated in vacuo to give a mixture of amine products; glc showed a 74 to 26 ratio of trans/cis (II/III) amines and $^1$H NMR verified this 3:1 ratio.

Example D

Enantioselective Synthesis of trans-1,2,3,5,6,10bR-Hexahydro-6S-[(4-methylthio)-phenyl]pyrrolo[2,1,-a]isoquinoline (Formula (I), Configuration (II): $R_4$,$R_5$,$R_6$,$R_7$ and $R_8$=H; $R_9$=4-methylthio)

While under an inert atmosphere, 1.5 mL of TFA was cooled to −10° C. and 250 mg (0.72 mmol) of aminoalcohol•HCl of formula (VII) where $R_4$, $R_5$, $R_6$, $R_7$ and $R_8$ are hydrogen and $R_9$ is 4-methylthio (prepared from 98% enantiomeric excess R-2-phenylpyrrolidine) was added. The reaction mixture turned a dark purple color which slowly disappeared over 1 hr. While maintaining a −10° to −5° C. reaction temperature, 1.3 mL (1.16 mmol) of $BH_3$•THF was added dropwise over 20 min. The reaction was allowed to warm to RT over 30 min and 3 mL of distilled water was added. After stirring for 1.5 hr the mixture was diluted with 5 mL of $CH_2Cl_2$ and the layers separated. The organic layer was washed with 1N NaOH (2×3 mL), dried with sodium sulfate, filtered, and rotovapped to afford 270 mg of the title compound as a thick oil. High field $^1$H NMR revealed that 10% of the unwanted diastereomer was present. Enantiomeric purity was found to be >95%.

Example E

Sodium Borohydride as the Reducing Agent
trans-1,2,3,5,6,10b-Hexahydro-6-phenyl pyrrolo[2,1-a]isoquinoline (Formula (I), configuration (II): $R_4$, $R_5$, $R_6$, $R_7$ $R_8$ and $R_9$=H)

45 mg of trans-1,2,3,5,6,10b-hexahydro-6-hydroxy-6-phenyl-pyrrolo[2,1-a]isoquinoline•HBr was dissolved in 1 mL of TFA under argon and stirred at RT for 30 min (to ensure that all substrate was in the iminium tautomeric form). The solution was cooled in an ice bath and 38 mg (1 mmol) of NaBH₄ pellets are added and stirred at approximately 5° C. It took approximately 15 min for the NaBH₄ pellets to be consumed. GLC examination at this point showed reduction completed with a trans/cis ratio of 87:13. The reaction was quenched with several drops of H₂O and stirred at approximately 10° C. for 1 hr. The reaction mixture was basified to a pH greater than 11 with 3N NaOH and extracted into CH₂Cl₂. The CH₂Cl₂ was dried (K₂CO₃) and evaporated in vacuo to give 27 mg of the title product as a yellow oil.

$^1$H NMR looked excellent for the desired trans isomer with about 10-15% of the cis isomer.

What is claimed is:

1. An enammonium salt of the following formula (X):

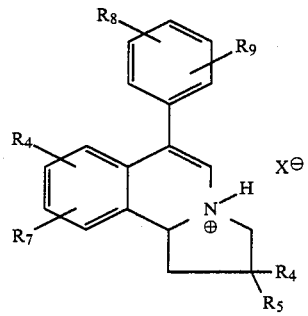

wherein $R_4$ and $R_5$ are the same and both are hydrogen, or different and each is selected from the group of hydrogen or lower alkyl;

$R_6$ and $R_7$ are the same or different and each is selected from the group hydrogen, lower alkyl, lower alkoxy, hydroxy, or halogen, or else are taken together as methylenedioxy; and $R_8$ and $R_9$ are selected from the group hydrogen, lower alkyl, perfluoro(lower)alkyl, lower alkoxy, carb(lower)alkoxy, lower alkylthio, lower alkylsulfonyl, nitro, or halogen; and X is an anion.

2. An iminium salt of the following formula (XI)

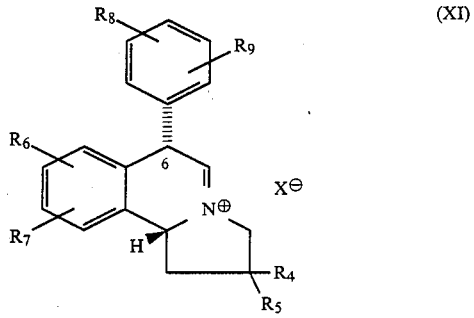

wherein $R_4$ and $R_5$ are the same and both are hydrogen, or different and each is selected from the group of hydrogen or lower alkyl;

$R_6$ and $R_7$ are the same or different and each is selected from the group hydrogen, lower alkyl, lower alkoxy, hydroxy, or halogen, or else are taken together as methylenedioxy; and $R_8$ and $R_9$ are selected from the group hydrogen, lower alkyl, perfluoro(lower)alkyl, lower alkoxy, carb(lower)alkoxy, lower alkylthio, lower alkylsulfonyl, nitro, or halogen; and X is an anion.

* * * * *